United States Patent [19]

Feldt

[11] 4,156,766

[45] May 29, 1979

[54] ACRYLIC POLYMERIZATION SYSTEMS AND DIACYL PEROXIDE CATALYSTS THEREFOR

[75] Inventor: Raymond J. Feldt, Belle Mead, N.J.

[73] Assignee: Johnson & Johnson, New Brunswick, N.J.

[21] Appl. No.: 832,304

[22] Filed: Sep. 12, 1977

Related U.S. Application Data

[62] Division of Ser. No. 758,277, Jan. 10, 1977, abandoned.

[51] Int. Cl.$^2$ ............................ C08F 4/32; C08F 4/34; C08F 22/14; C08K 9/06
[52] U.S. Cl. ................................ 526/313; 260/42.15; 260/42.17; 260/42.18; 526/211; 526/217; 526/232; 526/279
[58] Field of Search ............ 260/47 UA, 42.15, 42.17, 260/42.18, DIG. 36; 526/232, 313, 320, 211, 217, 279

[56] References Cited

U.S. PATENT DOCUMENTS

| | | | |
|---|---|---|---|
| 3,066,112 | 11/1962 | Bowen | 260/37 EP |
| 3,730,947 | 5/1973 | Stoffey et al. | 260/47 UA |
| 3,751,399 | 8/1973 | Lee et al. | 260/47 UA |
| 3,766,132 | 10/1973 | Lee et al. | 260/47 UA |
| 3,835,090 | 9/1974 | Gander et al. | 260/42.15 |

OTHER PUBLICATIONS

Chem. Abs. vol. 73 (1970) 110547y, "Low Temp. Polym. & Copoly. of Vinyl Chloride."

*Primary Examiner*—Herbert J. Lilling

[57] ABSTRACT

Acrylic polymerization systems having improved thermal stability are disclosed comprising an acrylic monomer binder, a diacyl peroxide catalyst selected from the group consisting of p-t-butylbenzoyl peroxide, 3,5-dimethylbenzoyl peroxide, and p-methylbenzoyl peroxide, and an amine accelerator for said catalyst. Several of the diacyl peroxide catalysts of the invention are novel.

16 Claims, No Drawings

ACRYLIC POLYMERIZATION SYSTEMS AND DIACYL PEROXIDE CATALYSTS THEREFOR

This a division of Application Ser. No. 758,277 filed Jan. 10, 1977, and now abandoned.

BACKGROUND OF THE INVENTION

The present invention pertains to acrylic polymerization systems and to diacyl peroxide catalysts useful in such systems, and particularly to such systems and catalysts used in dental restorations.

Acrylic polymerization systems are well-known in the art. They are described in, for example, Bowen U.S. Pat. No. 3,066,112; Lee, et al., U.S. Pat. No. 3,539,533; and Gander and Potts, U.S. Pat. No. 3,835,090, which are incorporated by reference into the present application. These systems are particularly useful as dental materials and generally comprise at least one liquid polymerizable acrylate or methacrylate monomer, a diacyl peroxide polymerization catalyst or initiator, and an amine accelerator for producing free radicals upon reaction with said catalyst thereby polymerizing the monomer. The systems may further comprise inorganic fillers and stabilizers.

These dental materials are generally prepared as two separate compositions for storage and distribution prior to use, one composition containing the catalyst and no activator and the other containing activator and no catalyst. These two compositions may be both liquid, both pastes, one liquid and one paste, one liquid and one solid, or the like. Conveniently, the two compositions may be both liquids (unfilled) or pastes (composite); the systems of the invention are thus exemplified.

In one type of system, each composition contains a liquid polymerizable monomer (also referred to as the binder) and an inorganic filler (if desired) as the major components. The first composition (denominated the "catalyst composition") contains in addition to these common ingredients an appropriate amount of a diacyl peroxide polymerization catalyst, typically benzoyl peroxide. The second composition (denominated the "activator composition" or "universal composition") contains in addition to these common ingredients an appropriate amount of an amine accelerator for the catalyst, typically N,N-bis-(2-hyydroxyethyl)-4-methylaniline in prior art activator compositions. Each composition usually further contains appropriate amounts of stabilizers to prevent polymerization or discoloration of the separate compositions prior to mixing or discoloration of the polymerized composition.

Polymerizable dental materials are used for a variety of applications. They may be used in direct filling of teeth to replace tooth structure which has decayed. They may be used to fill fissures in healthy teeth to prevent future decay. They may be used as glazing compounds over composite restorations to provide a smooth, glossy surface. They may be used as cement in the attachment of dental bridgework and the like to a tooth stump. They are well-known in the dental art as being superior dental materials, especially for anterior teeth.

A dental material should possess thermal stability during storage prior to use. Thus, while the material should gel in a relatively short time once the two compositions are mixed, they should be able to be stored as two separate compositions for an extended period of time, preferably for at least six months at room temperature. To achieve this stability, stabilizers are often added to prior art compositions to prevent premature polymerizations.

Prior art catalysts are generally diacyl peroxides as disclosed in Reinhardt U.S. Pat. No. 3,256,254 and Bafford U.S. Pat. No. 3,580,955, which latter describes methods of making some and provides a comprehensive list thereof. Because of their use of these prior art catalysts, prior art dental materials generally have poor thermal stability. That is, the individual catalyst compositions are not indefinitely stable, and may begin to polymerize even before they are mixed with an activator composition or may discolor, thereby providing material of unacceptable quality. Stabilizers are generally added to the catalyst compositions to increase its stability, but only a small amount of these can be added without adversely affecting the reactivity. The useful lifetime of the catalyst compositions of the prior art is approximately 6 to 10 months at 70° F.; at higher temperatures (e.g., 100° F.), it is even shorter. That the useful lifetime of prior art catalyst compositions is so short is a serious disadvantage thereof. This lact of thermal stability has led users of these restorative materials to keep them cooled to prolong their useful lifetime. That such cooling is necessary to prolong their useful lifetime is a further disadvantage of prior art acrylic restoration materials.

One who attempts to remedy this deficiency in thermal stability by altering the composition of the acrylic dental material must be careful, however not to impair the other desirable properties thereof. Thus, for example, it would be possible to extend the useful lifetime of catalyst compositions by adding greater amounts of stabilizer, but such would decrease the reactivity of the compositions when mixed with accelerator and consequently would increase the time between mixing and hardening of the polymer (the gel and set times), which increase is undesirable.

Although prior art polymerizable dental restorative materials have enjoyed success, especially in the area of highly filled restorations, they have had poor thermal stability.

It is therefore an object of the present invention to provide acrylic polymerization systems having improved thermal stability without impairing any of the presently-existing desirable qualities of the system.

It is a still further object to provide novel diacyl peroxides which may be used as catalysts in said acrylic polymerization systems, which catalysts provide improved thermal stability while at the same time not impairing other desirable properties of the system.

These and other objects of the present invention will become apparent as the detailed description thereof proceeds

SUMMARY OF THE INVENTION

There are provided by the present invention acrylic polymerization systems comprising at least one difunctional liquid polymerizable acrylate or methacrylate monomer; a diacyl peroxide catalyst selected from the group consisting of p-t-butylbenzoyl peroxide, 3,5-dimethylbenzoyl peroxide, and p-methylbenzoyl peroxide; and an amine accelerator for said catalyst. The peroxide catalysts p-t-butylbenzoyl peroxide and 3,5-dimethylbenzoly peroxide are novel and are a further aspect of the present invention.

The diacyl peroxide catalyst and amine accelerator are present in small amounts in the systems of the invention, typically from about 0.1% to about 3% each by weight of the weight of the liquid polymerizable monomer. Those skilled in the polymer art will readily understand how to determine the the effective and optimum amounts of these ingredients for a particular monomer (or monomer blend), diacyl peroxide catalyst, and amine accelerator.

The acrylic polymerization systems of the invention are substantially identical to those disclosed in the above-mentioned United States patents, which are incorporated herein by reference, with the improvement that one of the diacyl peroxide catalysts of the invention is substituted for the benzoyl peroxide used therein. Because of the increased thermal stability of the polymerization systems incorporating the catalysts of the invention, several advantages are achieved. In particular, the catalyst compositions of the acrylic polymerization systems of the invention, as a result of employing the diacyl benzoyl peroxide catalysts of the invention, have a useful lifetime of about 2 years at 70° F., which is defined herein as "good" thermal stability.

It is a surprising feature of the present invention that only these three diacyl peroxide catalysts, of all those tested, provided this increased thermal stability while not impairing other desirable properties of the system.

DETAILED DESCRIPTION OF THE INVENTION

The catalysts of the invention may be prepared by adding the appropriate acyl halide, preferably chloride, to an aqueous solution of alkali metal peroxide, preferably sodium peroxide, A slight molar excess of the peroxide is preferred.

The acyl chloride is preferably added as a solution in a small amount of an inert organic solvent such as, for example, benzene, toluene, xylene, or the like. After the reaction is complete, the desired product may be collected by filtration or the like. The preferred diacyl peroxide catalyst is p-t-butylbenzoyl peroxide. This compound and 3,5-dimethylbenzoyl peroxide are novel; it is intended that these two compounds be included within the scope of the present invention.

It is a surprising feature of the present invention that only the three diacyl peroxides of the invention, of all those tested, cause the catalyst compositions of the acrylic polymerization systems of the invention to have improved thermal stability and also acceptable reactivity. Homologs and analogs of the diacyl peroxides of the invention which were tested did not cause the same improvement in similar acrylic polymerization systems.

The thermally stable acrylic polymerization systems of the invention comprise a combination of at least one difunctional liquid polymerizable acrylate or methacrylate monomers as described in the above-mentioned United States patents and herein, a diacyl peroxide catalyst of the invention (preferably p-t-butylbenzoyl peroxide), and the amine accelerator.

Suitable amine accelerators useful in the thermally stable systems of the invention are, for example, those of formula:

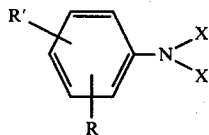

wherein R and R' may be either H or CH₃ and X may be CH₂CH₂OH, C₂H₅, or CH₃. A preferred accelerator is N,N-bis-(2-hydroxyethyl)-3,4-dimethylaniline.

The thermally stable acrylic polymerization systems of the invention are preferably utilized as two separate pastes, each preferably containing the same mixture of polymerizable monomers and each containing filler (if desired), one of the pastes containing a diacyl peroxide of the invention and no amine accelerator and other containing an amine accelerator and no peroxide catalyst. It is contemplated that the paste comprising polymerizable monomer, filler (if desired), stabilizer (if desired), and a diacyl peroxide of the invention is included within the scope of the present invention. Filler is preferably included in the systems of the invention.

The major portion of the systems of the invention comprises polymerizable monomer (or monomer plus filler if the latter is included), generally in excess of 90 percent of the weight of the composition. The catalyst, accelerator, and (if included) stabilizers make up only a small percentage of the weight of the composition, generally less than 10% and preferably less than 5% by weight of the weight of the composition. The catalyst of the invention is generally present in amounts ranging from about 0.1 percent to about 2.0 percent by weight, and more preferably from about 0.25 percent to about 1.0 percent by weight of the composition. These ranges are based upon the weight of the entire two-paste system; if one examines only the catalyst paste, then each of the above figures is generally doubled. Thus, for the catalyst paste, the catalyst is generally present in amounts ranging from about 2.0 percent to about 4.0 percent by weight, preferably from about 0.3 percent to about 3.0 percent by weight, and more preferably from about 0.5 percent to about 2.0 percent by weight of the weight of the catalyst paste.

The liquid polymerizable monomer in the systems of the invention may be, for example:

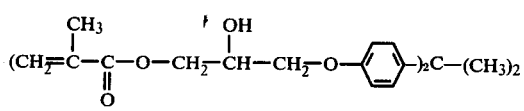

which is the glycidyl methacrylate derivative of bisphenol-A, hereinafter referred to as BIS-GMA; trimethacrylate and triacrylate esters of the aliphatic triols glycerol, trimethylolethane, trimethylolpropane, and trimethylolbutane; and the like. The latter group of materials may be exemplified by trimethylolpropane trimethacrylate (TMPTMA), trimethylolpropane triacrylate (TMPTA), and the like.

Other suitable acrylic monomer binders useful in any of the systems of the invention are, for example, bisphenol-A dimethyacrylate (BADM); triethyleneglycol dimethacrylate (TEGDM); methacrylic acid (MAA); 1,3-bis-[2,3-di(methacryloxy)propoxy]-benzene (RGTMA); 1,3-bis-(3-methacryloxy-2-hydroxypropoxy)-benzene (RGDMA), 2,2-bis-]4-(2-methacryloxyethoxy)phenyl]-propane (sold by Sartomer Division of Esschem Co. as SR-348); di-(2-methacryloxyethoxy)-diphenyl silane; di-(2-methacryloxymethylethoxy)-diphenyl silane; methacrylate esters (CMDPO-25 Methacrylate) in which a methacryloxy group or groups are attached to diphenyl oxide nuclei through single methylene bridges, the monomers being represented by the general formula:

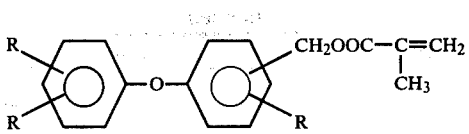

wherein R in each instance is at least one of the group consisting of H and

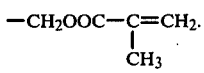

While the above monomers have been given by way of illustration, it should be understood that any difunctional liquid polymerizable acrylate or methacrylate monomer may be used. A preferred group of monomers comprises BIS-GMA, TEGDM, CMDPO-25 methacrylate, and trimethacrylate and triacrylate esters of the aliphatic triols glycerol, trimethylolethane, trimethylolpropane, and trimethylolbutane. Other monomers, such as monofunctional acrylate and methacrylate monomers, may be used in conjunction with the above difunctional monomers.

Stabilizers may be added to all systems, if desired, to inhibit the premature polymerization thereof during storage. Such stabilizers are generally free-radical chain reaction terminators such as, for example, a substituted phenol, exemplified by p-methoxyphenol, 2,6-di-t-butyl-4-methylphenol (known as BHT), a compound of formula:

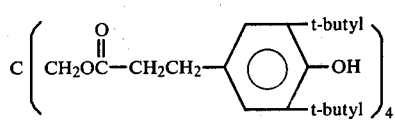

(sold by Geigy Chemical Company under the name Irganox 1010), and the like; or a stabilizer against ultraviolet-light-caused discoloration of the binder such as, for example, 2-hydroxy-4-methoxybenzophenone (sold by American Cyanamid under the name Cyasorb UV-9) or the like.

In addition to the above-described ingredients, all systems of the invention may further comprise an inorganic filler such as silica, glass beads, powdered glass, aluminum oxide, crystalline quartz, and the like. Such a filler would be included if the material of the invention were to be used, for example, in highly filled restorations, and would be treated with a suitable keying agent (e.g., silane-treated) as is known in the art.

One preferred system of the invention comprises from about 35 percent to about 90 percent by weight of a mixture of about 90 percent by weight BIS-GMA and about 10 percent by weight of bisphenol-A dimethacrylate (BADM), from about 65 percent to about 10 percent by weight of triethylene glycol dimethacrylate (TEGDM), from about 0.1 percent to about 2.0 percent by weight of a diacyl peroxide catalyst of the invention and from about 0.1 percent to about 2.0 percent by weight of an amine accelerator. A more preferred material comprises from about 70 percent to about 90 percent by weight of the aforementioned BIS-GMA and BADM mixture, from about 30 percent to about 10 percent by weight of TEGDM, from about 0.25 percent to about 1.50 percent by weight of diacyl peroxide catalyst, and from about 0.25 percent to about 1.5 percent by weight of an amine accelerator.

Another preferred system of the invention comprises from about 10 percent to about 90 percent by weight of CMDPO-25 methacrylate, from about 90 percent to about 10 percent by weight of trimethylolpropane trimethacrylate (TMPTMA), from about 0.2 percent to about 2.0 percent by weight of an amine accelerator and from about 0.2 percent to about 2.0 percent by weight of a diacyl peroxide catalyst of the invention. A more preferred material of this second type comprises from about 32 percent to about 42 percent by weight of CMDPO-25 methacrylate, from about 65 percent to about 55 percent by weight of trimethylolpropane trimethacrylate (TMPTMA), from about 0.25 to about 1.5 percent by weight of an amine accelerator, and from about 0.25 to about 1.5 percent by weight of diacyl peroxide catalyst.

Both of these preferred materials are preferably admixed with inorganic filler (e.g., silane-treated quartz, silane-treated glass, submicron silica, and the like), more preferably from about four to about five time their weight of inorganic filler.

The system of the invention is also preferably used as two compositions as previously discussed, one of which contains the accelerator and is free of peroxides (the accelerator composition), and one of which contains the diacyl peroxide catalyst free of the accelerator (the catalyst composition). These compositions, which may also contain a filler, are then mixed to initiate the polymerization reaction. The peroxide catalyst-containing compositions comprising a diacyl peroxide catalyst selected from the group consisting of p-t-butylbenzoyl peroxide, 3,5-dimethylbenzoyl peroxide, and p-methylbenzoyl peroxide are also considered to be part of the present invention.

One preferred catalyst composition of the invention thus comprises from about 35 percent to about 90 percent by weight of a mixture of about 90 percent by weight BIS-GMA and about 10 percent by weight of bisphenol-A dimethacrylate (BADM), from about 65 percent to about 10 percent by weight of triethylene glycol dimethacrylate (TEGDM), and from about 0.2 percent to about 4.0 percent by weight of a diacyl peroxide catalyst of the invention, and is essentially free of amine accelerators. A more preferred catalyst composition comprises from about 70 percent to about 90 percent by weight of the aforementioned BIS-GMA and BADM mixture, from about 30 percent to about 10 percent by weight of TEGDM and from about 0.5 percent to about 3.0 percent by weight of a diacyl peroxide of the invention and is essentially free of amine accelerators.

Another preferred catalyst composition of the invention comprises from about 10 percent to about 90 percent by weight of CMDPO-25 methacrylate, from about 90 percent to about 10 percent by weight of trimethylolpropane trimethacrylate (TMPTMA), and from about 0.4 percent to about 4.0 percent by weight of a diacyl peroxide catalyst of the invention, and is essentially free of amine accelerators. A more preferred accelerator composition of this second type comprises from about 32 percent to about 42 percent by weight of CMDPO-25 methacrylate, from about 65 percent to about 55 percent by weight of trimethylolpropane trimethacrylate (TMPTMA), and from about 0.50 to about 3.0 percent by weight of a diacyl peroxide of the invention and is essentially free of amine accelerators.

These preferred accelerator compositions are preferably admixed with inorganic filler (e.g., silane-treated quartz), more preferably from about four to about five times their weight of inorganic filler.

It should be understood throughout the above description of the systems of the invention that only 100% of the components may be present, despite the apparent possibility of slightly exceeding this amount if the maximum amount of each ingredient is selected.

The invention will be illustrated by the following examples, which are provided for illustrative purposes only and not to restrict the scope of the present invention, which scope is defined only in the appended claims. All parts are by weight unless otherwise specified.

EXAMPLE I p-t-Butylbenzoyl peroxide

To a solution of 1.95 g. of sodium peroxide in 23 ml. of distilled water maintained at 0°–5° C., is added dropwise with vigorous stirring a solution of 7.85 g. of p-t-butylbenzoyl chloride in 13 ml. of dry toluene. When the addition is complete after 45 minutes, the whole is allowed to stir for two and one-half hours at 0°–5° C., after which 80 ml. of cold water is added and the whole is stirred for an additional half hour at 0°–5° C. The resulting white precipitate is collected by filtration, washed with 55 ml. of cold methanol in three separate portions, and allowed to dry yield p-t-butylbenzoyl peroxide as a fine white powder; m.p. 149° C. (dec.)

EXAMPLE II

Following the procedure of Example I, but substituting for the p-t-butylbenzoyl chloride used therein an equivalent amount of the appropriately-substituted benzoyl chloride, there are produced p-methylbenzoyl peroxide (m.p. 132°–133° C. dec.) and 3,5-dimethylbenzoyl peroxide (m.p. 127°–128° C. dec.).

EXAMPLE III

Fused quartz is ground in a porcelain ball mill to a size that will pass through a 200-mesh screen. 500 g. of this ground quartz is placed in 1,000 ml. of 20% hydrochloric acid and heated to 80° C. for 1 hour. The acid is filtered off and the filler washed with water until the effluent reaches a pH of 6 to 7. The filler is dried in an open glass tray at 130° F. A water solution of silane is prepared by placing 0.4 ml. acetic acid and 10 g. of trimethoxysilylpropyl methacrylate in 200 g. of water and stirring rapidly at room temperature. A slurry is prepared of the filler and the silane solution and filtered. The solid thus obtained is placed in a glass tray and dried at 130° F. The material is stirred frequently during the drying process. This material is hereinafter referred to as "silane-treated quartz". Some of this silane-treated quartz is coated with a peroxide of the invention by dissolving the peroxide in acetone, mixing the acetone solution with the quartz, and evaporating the solvent. This peroxide-coated quartz is defined as "X%" peroxide-coated quartz, where "X%" is the weight of peroxide used in the coating process, as a percentage of the weight of the silane-treated quartz used.

Two pastes are prepared by mixing the following ingredients:

| | Paste A | Paste B |
|---|---|---|
| triethyleneglycol dimethylacrylate (TEGDM) | 2.24 | 2.24 |
| methacrylic acid (MAA) | 0.46 | 0.46 |
| 9:1 BIS-GMA:BADM | 19.0 | 19.0 |
| N,N-bis-(2-hydroxyethyl)-p-methylaniline | 0.34 | — |
| silane-treated quartz | 78.00 | — |
| 0.66% p-methylbenzoyl peroxide-coated quartz | — | 78.30 |
| | 100.04 | 100.00 |

Equal weights of each paste are combined and mixed with a spatula. After mixing for 30 seconds, the material gels in 98 seconds and becomes very hard in about four minutes. After twenty-four hours, the material has a flexural modulus of $2.1 \times 10^6$ and a Rockwell H hardness of 101, equivalent to physical characteristics of the identical pastes using the prior art benzoyl peroxide in place of the peroxide of the invention. The pastes are aged at 100° F. and are periodically tested for gel time; the peroxide-containing paste (Paste B) is tested for percent of original peroxide remaining undecomposed. The more stable the gel time and the greater the percent of peroxide remaining undecomposed, the better the thermal stability of the peroxide of the invention. The results are shown below in Table I.

EXAMPLE IV

Two pastes are prepared by mixing the following ingredients:

| | Paste A | Paste B |
|---|---|---|
| TEGDM | 2.24 | 2.24 |
| MAA | 0.46 | 0.46 |
| 9:1 BIS-GMA:BADM | 19.00 | 19.00 |
| N,N-bis-(2-hydroxyethyl)-p-methylaniline | 0.32 | — |
| silane-treated quartz | 78.00 | — |
| 0.7% 3,5-dimethylbenzoyl peroxide-coated quartz | — | 78.30 |
| | 100.02 | 100.00 |

The pastes are combined as in Example III. After 24 hrs. the resulting material has a flexural modulus of $1.7 \times 10^6$ and a Rockwell H hardness of 100 after gelling in 138 seconds and becoming very hard in 2-½ minutes. The peroxide-containing paste has good thermal stability as shown below in Table I.

EXAMPLE V

Two pastes are prepared by mixing the following ingredients:

| | Paste A | Paste B |
|---|---|---|
| TEGDM | 2.37 | 2.37 |
| MAA | 0.48 | 0.48 |
| BHT | 0.007 | 0.007 |
| Cyasorb UV-9 | 0.25 | 0.25 |
| 9:1 BIS-GMA:BADM | 20.00 | 20.00 |
| Submicron silica (hydrophobic) | 3.20 | 3.20 |
| N,N-bis-(2-hydroxyethyl)-p-methylaniline | 0.65 | — |
| silane-treated quartz | 79.90 | — |
| 1.2% p-tert.-butylbenzoyl peroxide-coated quartz | — | 80.80 |
| | 106.85 | 107.80 |

The composition formed by mixing the pastes has physical characteristics equivalent to the prior art composition using benzoyl peroxide. The pastes are aged and tested as in Example III; results are reported in Table I below.

EXAMPLE VI

Two pastes are prepared by mixing the following ingredients:

|  | Paste A | Paste B |
| --- | --- | --- |
| Trimethylolpropane triacrylate (TMPTA) | 2.00 | 2.00 |
| Cyasorb UV-9 | 0.02 | 0.02 |
| N,N-bis-(2-hydroxyethyl)-p-methylaniline | 0.07 | — |
| Submicron silica (hydrophobic) | 0.16 | 0.16 |
| silane-treated quartz | 9.66 | — |
| 1.1% p-methylbenzoyl peroxide-coated quartz | — | 9.66 |
|  | 11.91 | 11.84 |

These pastes are mixed and tested as in Example III. After 24 hours at composition has a flexural modulus of $2.5 \times 10^6$ and a Rockwell H hardness of 114 with a gel time of 130 seconds.

EXAMPLE VII

Two pastes are prepared by mixing the following ingredients:

|  | Paste A | Paste B |
| --- | --- | --- |
| CMDPO-25 methacrylate | 2.75 | 1.40 |
| Trimethylolpropane trimethacrylate (TMPTMA) | 4.35 | 2.18 |
| Cyasorb UV-9 | 0.07 | 0.034 |
| N,N-bis-(2-hydroxyethyl)-p-methylaniline | 0.144 | — |
| silane-treated quartz | 32.80 | — |
| 0.7% p-methylbenzoyl peroxide coated quartz | — | 16.47 |
|  | 40.114 | 20.61 |

These pastes are mixed and tested as in Example III. After 24 hours, the composition has a gel time of 122 seconds, a flexural modulus of $2.5 \times 10^6$, and a Rockwell H hardness of 112.

EXAMPLE VIII

Two pastes are prepared by mixing the following ingredients:

|  | Paste A | Paste B |
| --- | --- | --- |
| CMDPO-25 methacrylate | 0.39 | 0.78 |
| BIS-GMA | 0.21 | — |
| TMPTMA | 1.42 | 1.22 |
| Irganox 1010 | 0.005 | 0.005 |
| Cyasorb UV-9 | 0.01 | 0.01 |
| N,N-bis-(2-hydroxyethyl)-p-methylaniline | 0.06 | — |
| Submicron silica (hydrophobic) | 0.24 | 0.24 |
| silane-treated quartz | 9.82 | — |
| 1.2% p-t-butylbenzoyl peroxide-coated quartz | — | 9.94 |
|  | 12.16 | 11.10 |

The compositions formed by mixing the pastes have good hardness characteristics.

EXAMPLE IX

Two pastes are prepared by mixing the following ingredients:

|  | Paste A | Paste B |
| --- | --- | --- |
| 90:10 BIS-GMA:BADM | 24.0 | 24.0 |
| triethyleneglycol dimethacrylate (TEGDM) | 2.8 | 2.8 |
| methacrylic acid (MAA) | 0.6 | 0.6 |
| BHT | 0.04 | 0.04 |
| Cyasorb UV-9 | 0.3 | 0.3 |
| N,N-bis-(2-hydroxyethyl)-p-methylaniline | 0.60 | — |
| Submicron silica (hydrophobic) | 3.84 | 3.84 |
| silane-treated quartz | 95.70 | — |
| 1.2% p-t-butybenzoyl peroxide-coated quartz | — | 97.00 |
|  | 127.88 | 128.58 |

These pastes are tested for gel time and percent peroxide remaining in Paste B after aging for various periods; these data are reported in Table I.

EXAMPLE X

For comparison with Example IX, two identical pastes to those prepared therein are made, except using 0.39 parts of N,N-bis-(2-hydroxyethyl)-p-methylaniline instead of the 0.60 parts used therein and substituting 19.4 parts of silane-treated quartz and 77.60 parts of 0.68% benzoyl peroxide-coated quartz for the p-t-butylbenzoyl peroxide-coated quartz used therein. The aging data are reported below in Table I.

EXAMPLE XI

Two pastes are prepared by mixing the following ingredients:

|  | Paste A | Paste B |
| --- | --- | --- |
| 9:1 BIS-GMA:BADM | 10.00 | 20.00 |
| TEGDM | 1.19 | 2.38 |
| MAA | 0.24 | 0.48 |
| BHT | 0.008 | 0.016 |
| Cyasorb UV-9 | 0.12 | 0.24 |
| N,N-bis-(2-hydroxyethyl)-3,4-dimethylaniline | 0.30 | — |
| Submicron silica (hydrophobic) | 1.60 | 3.20 |
| 1.2% p-t-butylbenzoyl peroxide-coated quartz | — | 80.80 |
| silane-treated quartz | 39.85 | — |
|  | 53.31 | 106.12 |

The composition formed by mixing and pastes has good hardness and surface cure. The pastes are aged and tested as in Example III, results are reported in Table I below.

EXAMPLE XII

Two pastes are prepared by mixing the following ingredients:

|  | Paste A | Paste B |
| --- | --- | --- |
| 9:1 BIS-GMA:BADM | 10.00 | 20.00 |
| TEGDM | 1.18 | 2.37 |
| MAA | 0.24 | 0.48 |
| BHT | 0.01 | 0.02 |
| Cyasorb UV-9 | 0.12 | 0.24 |
| N,N-bis-(2-hydroxyethyl)-3,4-dimethylaniline | 0.35 | — |
| Submicron silica (hydrophobic) | 1.60 | 3.20 |
| 1.2% p-methylbenzoyl | | |

-continued

|  | Paste A | Paste B |
|---|---|---|
| peroxide-coated quartz | — | 80.80 |
| silane-treated quartz | 39.97 | — |
|  | 53.47 | 107.11 |

The composition formed by mixing the pastes has good hardness and surface cure. The pastes are aged and tested as in Example III; results are reported in Table I below.

Below are reported gel times and percent peroxide remaining for compositions and peroxide pastes of the invention prepared in some of the above examples after being aged at 100° F. or 120° F. For comparison, pastes equivalent to those of Example III, but having benzoyl peroxide as catalyst, have only 53% peroxide remaining after being aged at 100° F. for 91 days and only 48% remaining after being aged at 120° F. for 49 days.

TABLE I

| Example | Aged(Days) | Temperature(°F.) | Gel Time(Sec.) | % Peroxide |
|---|---|---|---|---|
| III | 0 | 100 | 98 | 100 |
|  | 54 | 100 | 98 | 85 |
|  | 96 | 100 | 117 | 76 |
| IV | 0 | 100 | 138 | 100 |
|  | 54 | 100 | 115 | 82 |
|  | 96 | 100 | 163 | 77 |
| V | 0 | 120 | 99 | 100 |
|  | 49 | 120 | 100 | 84 |
|  | 126 | 120 | 137 | 59 |
|  | 154 | 120 | 180 | 51 |
| IX | 0 | 100 | 103 | 100 |
|  | 91 | 100 | 107 | 89 |
|  | 210 | 100 | 115 | 79 |
| X | 0 | 100 | 121 | 100 |
|  | 42 | 100 | 135 | 75 |
|  | 91 | 100 | 190 | 53 |
| XI | 0 | 120 | 70 | 100 |
|  | 43 | 120 | 65 | 78 |
|  | 85 | 120 | 84 | 65 |
|  | 120 | 120 | 72 | 52 |
| XII | 0 | 120 | 114 | 100 |
|  | 43 | 120 | 45 | 72 |
|  | 85 | 120 | 60 | 55 |
|  | 120 | 120 | 106 | 41 |

The above Examples are given by way of illustration only and not to limit the scope of the present invention, which scope is defined by the appended claims.

What is claimed is:

1. A dental restorative material having improved thermal stability which comprises:
   (a) at least one difunctional liquid, polymerizable monomer selected from the group consisting of BIS-GMA; triethylene glycol dimethacrylate (TEGDM); trimethacrylate and triacrylate esters of the aliphatic triols glycerol, trimethylolethane, trimethylolpropane, and trimethylolbutane; and methacrylate esters (CMDPO-25 methacrylate) in which a methacryloxy group or groups are attached to diphenyl oxide nuclei through single methylene bridges, the monomers being represented by the general formula:

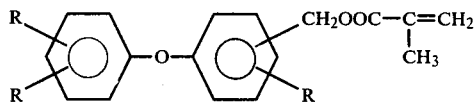

wherein R in each instance is at least one of the group consisting of H and $$-CH_2-OOC-C=CH_2.$$
$$\phantom{-CH_2-OOC-}|$$
$$\phantom{-CH_2-OOC-}CH_3$$

(b) a diacyl peroxide catalyst consisting of p-t-butylbenzoyl peroxide; and
   (c) an amine accelerator for said catalyst.

2. The material of claim 1, which further comprises an inorganic filler.

3. The material of claim 1, wherein the diacyl peroxide catalyst is present in an amount from about 0.1 percent to about 2.0 percent by weight of the weight of the material.

4. The material of claim 1, wherein the diacyl peroxide catalyst is present in an amount from about 0.25 percent to about 1.0 percent by weight of the weight of the material.

5. The material of claim 1, which comprises from about 35 percent to about 90 percent by weight of a mixture of about 90 percent by weight BIS-GMA and about 10 percent by weight bisphenol-A dimethacrylate (BADM); from about 65 percent to about 10 percent by weight of triethylene glycol dimethacrylate (TEGDM); from about 0.1 percent to about 2.0 percent by weight of diacyl peroxide catalyst, and from about 0.1 percent to about 2.0 percent by weight of amine accelerator.

6. The material of claim 5, which comprises from about 70 percent to about 90 percent by weight of said BIS-GMA and bisphenol-A dimethacrylate (BADM) mixture; from about 30 percent to about 10 percent by weight of triethylene glycol dimethacrylate (TEGDM); from about 0.25 percent to about 1.5 percent by weight of diacyl peroxide catalyst; and from about 0.25 percent to about 1.5 percent by weight of amine accelerator.

7. The material of claim 1, which comprises from about 10 percent to about 90 percent by weight of CMDPP-25 methacrylate, from about 90 percent to about 10 percent by weight of trimethylolpropane trimethyacrylate (TMPTMA), from about 0.2 percent to about 2.0 percent by weight of amine accelerator, from about 0.2 percent to about 2.0 percent by weight of diacyl peroxide catalyst, and is admixed with from about four to about five times its weight of an inorganic filler.

8. The material of claim 7, which comprises from about 32 percent to about 42 percent by weight of CMDPO-25 methacrylate, from about 65 percent to about 55 percent by weight of trimethylolpropane trimethacrylate (TMPTMA), from about 0.25 to about 1.5 percent by weight of amine accelerator, and from about 0.25 to about 1.5 percent by weight of diacyl peroxide catalyst.

9. A composition useful in dental restoration and having improved thermal stability which comprises:
   (a) at least one difunctional liquid, polymerizable monomer selected from the group consisting of BIS-GMA; triethylene glycol dimethacrylate (TEGDM); trimethacrylate and triacrylate esters of the aliphatic triols glycerol, trimethylolethane, trimethylolpropane, and trimethylolbutane; and methacrylate esters (CMDPO-25 methacrylate) in which a methacryloxy group or groups are attached to diphenyl oxide nuclei through single methylene bridges, the monomers being represented by the general formula:

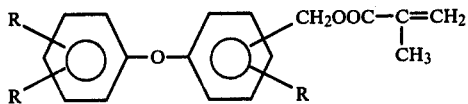

wherein R in each instance is at least one of the group consisting of H and

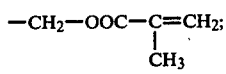

and (b) a diacyl peroxide catalyst consisting of p-t-butylbenzoyl peroxide, said composition being essentially free of accelerators for said catalyst.

10. The composition of claim 9, which further comprises an inorganic filler.

11. The compositon of claim 9, wherein the diacyl peroxide catalyst is present in an amount from about 0.2 percent to about 4.0 percent by weight of the weight of the composition.

12. The composition of claim 9, wherein the diacyl peroxide catalyst is present in an amount from about 0.5 percent to about 2.0 percent by weight of the weight of the composition.

13. The composition of claim 9, which comprises from about 35 percent to about 90 percent by weight of a mixture of about 90 percent by weight BIS-GMA and about 10 percent by weight of bisphenol-A dimethacrylate (BADM); from about 65 percent to about 10 percent by weight of triethyleneglycol dimethacrylate (TEGDM); and from about 0.2 percent to about 4.0 percent by weight of diacyl peroxide catalyst.

14. The composition of claim 13, which comprises from about 70 percent to about 90 percent by weight of said BIS-GMA and RADM mixture; from about 30 percent to about 10 percent of said TEGDM; and from about 0.5 percent to about 3.0 percent by weight of diacyl peroxide catalyst.

15. The composition of claim 9, which comprises from about 10 percent to about 90 percent by weight of CMPDO-25 -methacrylate, from about 90 percent to about 10 percent by weight of trimethylolpropane trimethacrylate (TMPTMA), and from about 0.4 percent to about 4.0 percent by weight of diacyl peroxide catalyst.

16. The composition of claim 15, which comprises from about 32 percent to about 42 percent by weight of CMPDO-25 methacrylate, from about 65 percent to about 55 percent by weight of trimethylolpropane trimethacrylate (TMPTMA), and from about 0.5 to about 3.0 percent by weight diacyl peroxide catalyst.

* * * * *

UNITED STATES PATENT AND TRADEMARK OFFICE
CERTIFICATE OF CORRECTION

PATENT NO. : 4,156,766
DATED : May 29, 1979
INVENTOR(S) : Raymond John Feldt

It is certified that error appears in the above-identified patent and that said Letters Patent are hereby corrected as shown below:

In Column 2, line 7, "some" should read -- same --.

In Column 2, line 22, "lact" should read -- lack --.

In Column 2, line 54, "proceeds" should read -- proceeds. --.

In Column 4, line 9, "and other" should read -- and the other --.

In Column 4, line 60, "bis-]4-" should read -- bis-[4- --.

In Column 8, line 67, "107.80" should read -- 107.10 --.

In Column 10, line 51, "mixing and pastes" should read -- mixing the pastes --.

In Column 12, line 39, "CMDPP-25" should read -- CMDPO-25 --.

In Column 14, line 11, "RADM" should read -- BADM --.

In Column 14, line 15, "25-methacrylate" should read -- 25 methacrylate --.

Signed and Sealed this

Sixteenth Day of October 1979

[SEAL]

Attest:

RUTH C. MASON
Attesting Officer

LUTRELLE F. PARKER
Acting Commissioner of Patents and Trademarks